US012575851B2

(12) United States Patent
Akagane

(10) Patent No.: US 12,575,851 B2
(45) Date of Patent: Mar. 17, 2026

(54) VIBRATION TRANSMISSION MEMBER, ULTRASONIC TREATMENT INSTRUMENT, AND METHOD OF MANUFACTURING VIBRATION TRANSMISSION MEMBER

(71) Applicant: OLYMPUS CORPORATION, Hachioji (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 809 days.

(21) Appl. No.: 17/873,408

(22) Filed: Jul. 26, 2022

(65) Prior Publication Data

US 2022/0354529 A1     Nov. 10, 2022

Related U.S. Application Data

(63) Continuation of application No. PCT/JP2020/002847, filed on Jan. 27, 2020.

(51) Int. Cl.
*A61B 17/32* (2006.01)
*A61B 17/00* (2006.01)

(52) U.S. Cl.
CPC .............. *A61B 17/320092* (2013.01); *A61B 2017/00526* (2013.01); *A61B 2017/00831* (2013.01);
(Continued)

(58) Field of Classification Search
CPC .. A61B 17/320092; A61B 2017/00526; A61B 2017/00831; A61B 2017/2825;
(Continued)

(56) References Cited

U.S. PATENT DOCUMENTS

2009/0143806 A1* 6/2009 Witt ...................... A61L 31/08
427/2.28
2016/0374744 A1 12/2016 Akagane
(Continued)

FOREIGN PATENT DOCUMENTS

WO     2016/163450 A1     10/2016
WO     2018/037478 A1     3/2018
WO     2020/016974 A1     1/2020

OTHER PUBLICATIONS

Mar. 17, 2020 International Search Report issued in International Patent Application No. PCT/JP2020/002847.

*Primary Examiner* — Tigist S Demie
(74) *Attorney, Agent, or Firm* — Oliff PLC

(57) ABSTRACT

A vibration transmission member includes a main body, a treatment portion that is provided at the distal end of the main body, a first covering formed of a material that has an electrical insulating property and has a thermal conductivity lower than a thermal conductivity of the main body, which covers a part of a surface of the treatment portion, and a second covering formed of a material that has an electrical insulating property and has a thermal conductivity lower than the thermal conductivity of the main body. The second covering is integrally formed with at least a part of the first covering and varies in thickness in a circumferential direction of the main body. The second covering includes a first area and a second area in the circumferential direction, such that a thickness dimension of the first area is smaller than a thickness dimension of the second area.

19 Claims, 10 Drawing Sheets

(52) U.S. Cl.
CPC ............. *A61B 2017/320082* (2017.08); *A61B 2017/320094* (2017.08)

(58) Field of Classification Search
CPC ......... A61B 2017/320082; A61B 2017/32009; A61B 2017/320094
See application file for complete search history.

(56)                References Cited

U.S. PATENT DOCUMENTS

2018/0042638 A1     2/2018  Hirai et al.
2019/0183522 A1*    6/2019  Akagane ................ A61B 17/00

* cited by examiner

VIBRATION TRANSMISSION MEMBER, ULTRASONIC TREATMENT INSTRUMENT, AND METHOD OF MANUFACTURING VIBRATION TRANSMISSION MEMBER

CROSS-REFERENCE TO RELATED APPLICATION

This application is a continuation of International Application No. PCT/JP2020/002847, filed on Jan. 27, 2020, the entire contents of which are incorporated herein by reference.

BACKGROUND

1. Technical Field

The present disclosure relates to a vibration transmission member, an ultrasonic treatment instrument, and a method of manufacturing the vibration transmission member.

2. Related Art

In the related art, there has been known an ultrasonic treatment instrument that applies ultrasonic vibration to a region (hereinafter, described as a target region) to be joined and incised in a living tissue to performs joining and incision on the target region.

This ultrasonic treatment instrument includes a vibration transmission member that transmits ultrasonic vibration from a proximal end toward a distal end and applies the ultrasonic vibration to a target region from a treatment surface provided at the distal end to treat the target region.

Incidentally, in a case where the target region is treated by application of ultrasonic vibration, a temperature of an outer surface of the vibration transmission member other than the treatment surface also increases. Then, in a case where the outer surface comes into contact with a region other than the target region in a living tissue in a state where the temperature of the outer surface is high, an unintended effect is exerted on the living tissue.

In this regard, in the known ultrasonic treatment instrument, a coating is formed on the outer surface of the vibration transmission member other than the treatment surface to avoid the unintended effect on the living tissue.

SUMMARY

In some embodiments, a vibration transmission member includes: a main body configured to transmit ultrasonic vibration from a proximal end toward a distal end of the main body; a treatment portion that is provided at the distal end of the main body, the treatment portion being configured to apply ultrasonic vibration to a living tissue; a first covering formed of a material that has an electrical insulating property and has a thermal conductivity lower than a thermal conductivity of the main body, the first covering covering a part of a surface of the treatment portion; and a second covering formed of a material that has an electrical insulating property and has a thermal conductivity lower than the thermal conductivity of the main body, the second covering being integrally formed with at least a part of the first covering. The second covering varies in thickness in a circumferential direction of the main body, the second covering includes at least a first area, which is located in a region of the second covering where a stress concentrates, and a second area in the circumferential direction, which are defined by different thicknesses, a thickness dimension of the first area is smaller than a thickness dimension of the second area of the second covering.

In some embodiments, an ultrasonic treatment instrument includes: a vibration transmission member configured to transmit ultrasonic vibration; and a jaw configured to grip a living tissue between the jaw and the vibration transmission member. The vibration transmission member includes a main body configured to transmit the ultrasonic vibration from a proximal end toward a distal end of the main body, a treatment portion that is provided at the distal end of the main body, the treatment portion being configured to grip the living tissue between the treatment portion and the jaw, and the treatment portion being configured to apply the ultrasonic vibration to the living tissue, a first covering formed of a material that has an electrical insulating property and has a thermal conductivity lower than a thermal conductivity of the main body, the first covering covering a part of a surface of the treatment portion, and a second covering formed of a material that has an electrical insulating property and has a thermal conductivity lower than the thermal conductivity of the main body. The second covering is integrally formed with at least a part of the first covering, the second covering varying in thickness in a circumferential direction of the main body, the second covering including at least a first area, which is located in a region of the second covering where a stress concentrates, and a second area in the circumferential direction, which are defined by different thicknesses, and a thickness dimension of the first area is smaller than a thickness dimension of the second area of the second covering.

In some embodiments, provided is a method of manufacturing a vibration transmission member including a main body configured to apply ultrasonic vibration to a living tissue from a treatment portion provided at a distal end of the main body. The method includes: forming a first covering that covers a part of a surface of the treatment portion by using a material having an electrical insulating property and a thermal conductivity lower than a thermal conductivity of the main body; and performing bonding to the first covering by heat treatment to form a second covering on at least a part of the first covering by using a material having an electrical insulating property and a thermal conductivity lower than the thermal conductivity of the main body, the second covering being formed by making a thickness dimension of a first area smaller than a thickness dimension of a second area of the second covering. The second covering varies in thickness in a circumferential direction of the main body, and the second covering includes, in the circumferential direction, at least (i) the first area, which is located in a region of the second covering where a stress concentrates, and (ii) the second area, which are defined by different thicknesses.

The above and other features, advantages and technical and industrial significance of this disclosure will be better understood by reading the following detailed description of presently disclosed embodiments of the disclosure, when considered in connection with the accompanying drawings.

DETAILED DESCRIPTION

Figure 1:
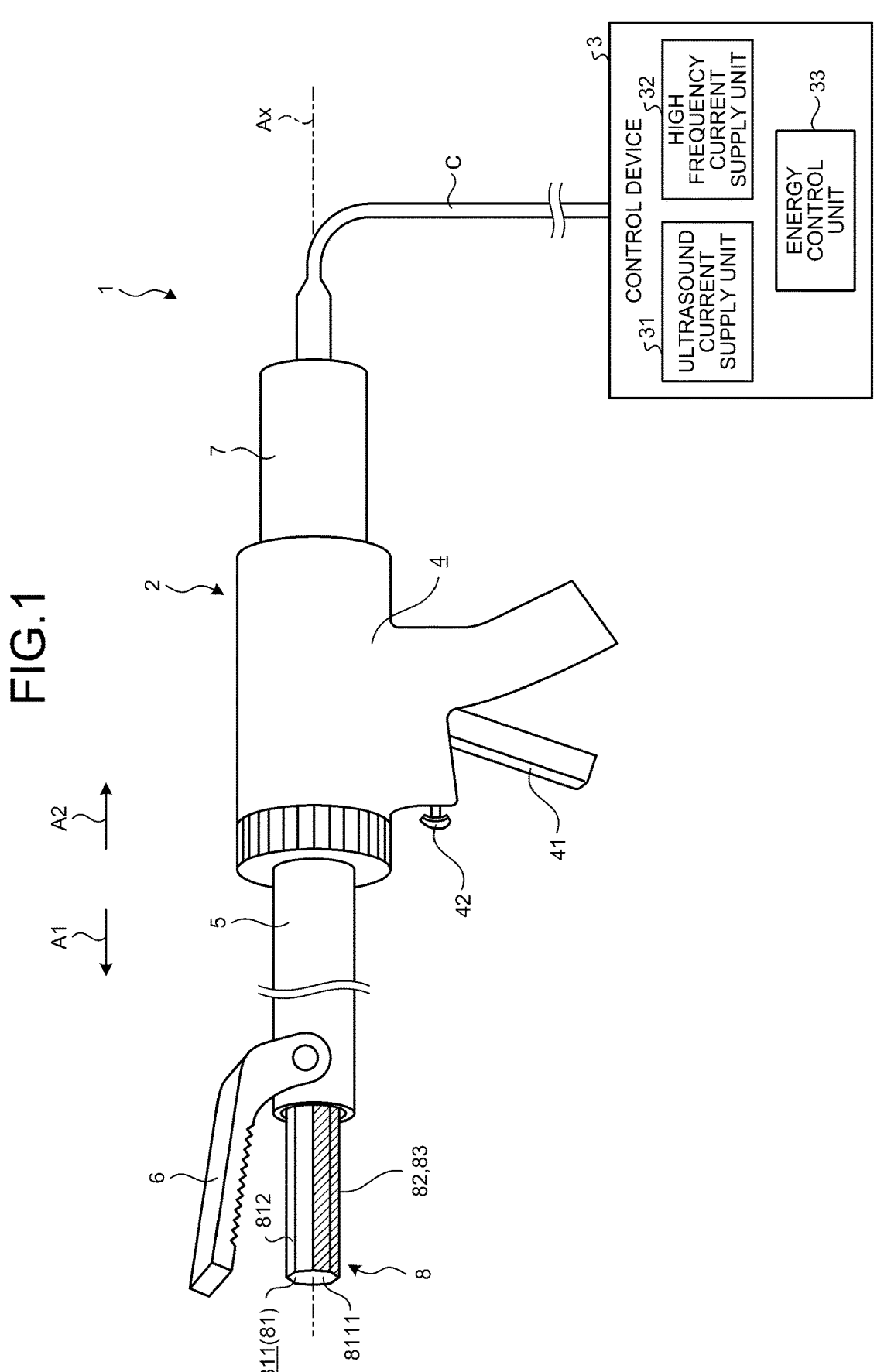
FIG. 1 is a view illustrating a treatment device according to a first embodiment.

Hereinafter, modes for carrying out the disclosure (embodiments) will be described with reference to the drawings. Note that the disclosure is not limited by the embodiments described below. Furthermore, in the description of the drawings, the same portions are denoted by the same reference numerals.

First Embodiment

Schematic Configuration of Treatment Device

FIG. 1 is a view illustrating a treatment device 1 according to a first embodiment.

The treatment device 1 applies ultrasonic energy and high frequency energy to a treatment target region (hereinafter, described as a target region) in a living tissue to treat the target region. Here, the treatment means, for example, coagulation and incision of the target region. As illustrated in FIG. 1, the treatment device 1 includes an ultrasonic treatment instrument 2 and a control device 3.

The ultrasonic treatment instrument 2 is, for example, a medical treatment instrument using a bolted Langevin transducer (BLT) for treating the target region in the state of passing through an abdominal wall. As illustrated in FIG. 1, the ultrasonic treatment instrument 2 includes a handle 4, a sheath 5, a jaw 6, a transducer unit 7, and a vibration transmission member 8.

The handle 4 is a portion which an operator holds with their hand. Then, as illustrated in FIG. 1, the handle 4 is provided with an operation knob 41 and an operation button 42.

The sheath 5 has a cylindrical shape. Note that hereinafter, the central axis of the sheath 5 is referred to as a central axis Ax (FIG. 1). In addition, hereinafter, one side along the central axis Ax is referred to as a distal end side A1 (FIG. 1), and the other side is referred to as a proximal end side A2 (FIG. 1). Then, the sheath 5 is attached to the handle 4 by inserting a part of the proximal end side A2 into the handle 4 from the distal end side A1 of the handle 4.

The jaw 6 is rotatably attached to the end portion of the sheath 5 on the distal end side A1, and the target region is gripped between the jaw 6 and the portion of the vibration transmission member 8 on the distal end side A1. Note that an opening and closing mechanism (not illustrated) for opening and closing the jaw 6 with respect to the portion of the vibration transmission member 8 on the distal end side A1 according to the operation of the operation knob 41 by the operator is provided inside the handle 4 and the sheath 5 described above.

In the jaw 6, a pad 61 (see FIG. 5) made of resin is attached to a surface facing the vibration transmission member 8. Since the pad 61 has an insulating property, the pad has a function of preventing a short circuit between the jaw 6 and the vibration transmission member 8. In addition, the pad 61 has a function of preventing the vibration transmission member 8, which is ultrasonically vibrating, from being damaged by colliding with the jaw 6 when the incision of the target region by the ultrasonic vibration is completed.

Figure 2:
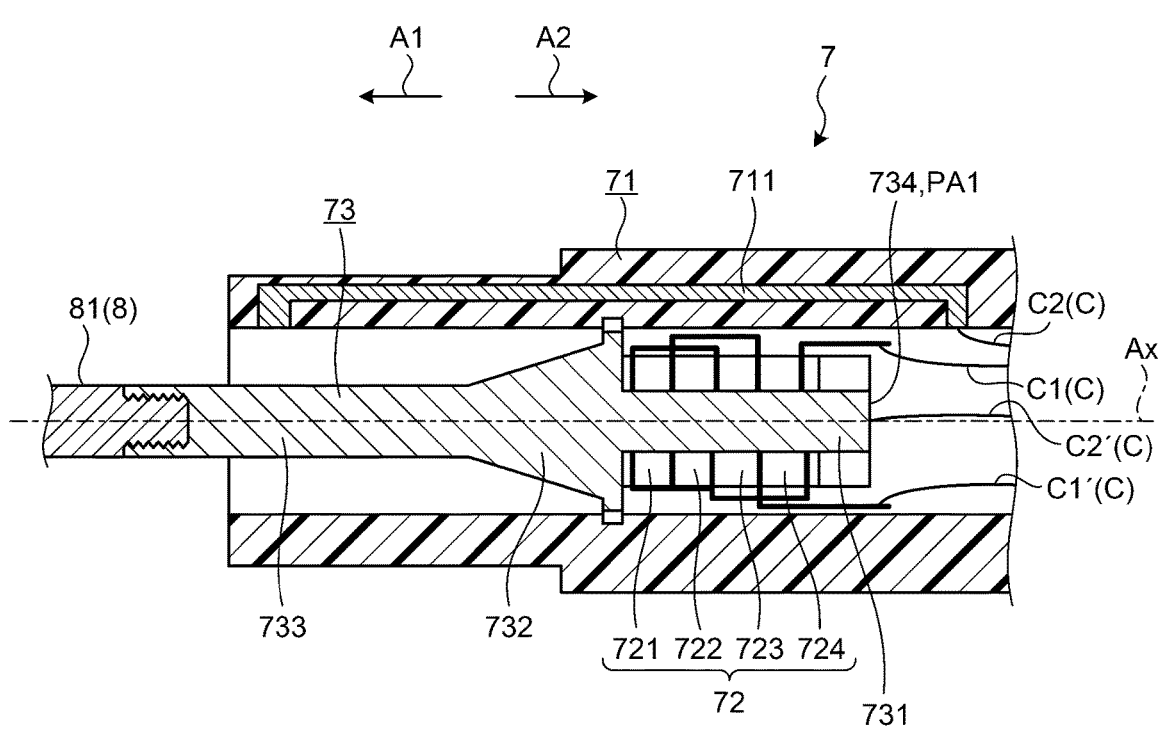
FIG. 2 is a cross-sectional view illustrating a transducer unit.

FIG. 2 is a cross-sectional view illustrating the transducer unit 7. Specifically, FIG. 2 is a cross-sectional view of the transducer unit 7 taken along a plane including the central axis Ax.

As illustrated in FIG. 2, the transducer unit 7 includes a transducer case 71, an ultrasonic transducer 72, and a horn 73.

The transducer case 71 extends linearly along the central axis Ax, and is attached to the handle 4 by inserting a part of the distal end side A1 into the handle 4 from the proximal end side A2 of the handle 4. Then, in a state where the transducer case 71 is attached to the handle 4, the end portion on the distal end side A1 is connected to the end portion of the sheath 5 on the proximal end side A2.

The ultrasonic transducer 72 is housed inside the transducer case 71 and generates ultrasonic vibration under the control of the control device 3. In the first embodiment, the ultrasonic vibration is longitudinal vibration which vibrates in a direction along the central axis Ax. As illustrated in FIG. 2, the ultrasonic transducer 72 is a BLT including a plurality of piezoelectric elements 721 to 724 stacked along the central axis Ax. Note that in the first embodiment, four piezoelectric elements 721 to 724 are provided, but the number of piezoelectric elements is not limited to four, and another number of piezoelectric elements may be used.

The horn 73 is housed inside the transducer case 71 and expands the amplitude of the ultrasonic vibration generated by the ultrasonic transducer 72. The horn 73 has an elongated shape extending linearly along the central axis Ax. Then, as illustrated in FIG. 2, the horn 73 includes a first attachment portion 731 to which the ultrasonic transducer 72 is attached from the proximal end side A2 toward the distal end side A1, a cross-sectional area changing portion 732 which has a shape in which a cross-sectional area decreases toward the distal end side A1 and expands the amplitude of the ultrasonic vibration, and a second attachment portion 733 to which the vibration transmission member 8 is attached.

The vibration transmission member 8 has an elongated shape extending linearly along the central axis Ax, and is inserted into the sheath 5 in a state where a portion on the distal end side A1 protrudes to the outside as illustrated in FIG. 1. In addition, as illustrated in FIG. 2, the end portion of the vibration transmission member 8 on the proximal end side A2 is connected to the second attachment portion 733. Then, the vibration transmission member 8 transmits the ultrasonic vibration, which has been generated by the ultrasonic transducer 72 and passed through the horn 73, from the end portion on the proximal end side A2 to the end portion on the distal end side A1 and applies the ultrasonic vibration to the target region gripped between the end portion on the distal end side A1 and the jaw 6 to treat the target region. That is, the target region is treated by application of ultrasonic energy from the end portion on the distal end side A1. Note that the detailed configuration of the vibration transmission member 8 will be described later.

The control device 3 is electrically connected to the ultrasonic treatment instrument 2 by an electric cable C (FIG. 1), and comprehensively controls the operation of the ultrasonic treatment instrument 2. As illustrated in FIG. 1, the control device 3 includes an ultrasonic current supply unit 31, a high frequency current supply unit 32, and an energy control unit 33.

Here, as illustrated in FIG. 2, a pair of transducer lead wires C1 and C1' configuring the electric cable C is joined to the ultrasonic transducer 72.

Then, the ultrasonic current supply unit 31 supplies AC power to the ultrasonic transducer 72 via the pair of transducer lead wires C1 and C1' under the control of the energy control unit 33. As a result, the ultrasonic transducer 72 generates ultrasonic vibration.

Here, as illustrated in FIG. 2, the transducer case 71 is provided with a first conductive portion 711 extending from the end portion on the proximal end side A2 to the end portion on the distal end side A1. In addition, although not specifically illustrated, the sheath 5 is provided with a second conductive portion extending from the end portion on the proximal end side A2 to the end portion on the distal end side A1 and electrically connects the first conductive portion 711 and the jaw 6. Further, a high frequency lead wire C2 configuring the electric cable C is joined to the end portion of the first conductive portion 711 on the proximal end side A2. Further, a high frequency lead wire C2' configuring the electric cable C is joined to the first attachment portion 731.

Under the control of the energy control unit 33, the high frequency current supply unit 32 supplies a high frequency current between the jaw 6 and the vibration transmission member 8 via the pair of high frequency lead wires C2 and C2', the first conductive portion 711, the second conductive portion, and the horn 73. As a result, a high frequency current flows through the target region gripped between the jaw 6 and the portion of the vibration transmission member 8 on the distal end side A1. That is, high frequency energy is applied to the target region. Then, in the target region, Joule heat is generated by the high frequency current flowing therethrough, and the target region is treated.

As described above, the jaw 6 and the vibration transmission member 8 also function as a high frequency electrode. In other words, the ultrasonic treatment instrument 2 also functions as a bipolar treatment instrument when the jaw 6 and the vibration transmission member 8 function as a pair of high frequency electrodes.

The energy control unit 33 is, for example, a central processing unit (CPU), a field-programmable gate array (FPGA), or the like, and controls the operation of the ultrasonic current supply unit 31 and the high frequency current supply unit 32 in a case where the operation button 42 is pressed by the operator.

Configuration of Vibration Transmission Member

Next, the detailed configuration of the above-described vibration transmission member 8 will be described.

Figure 3:
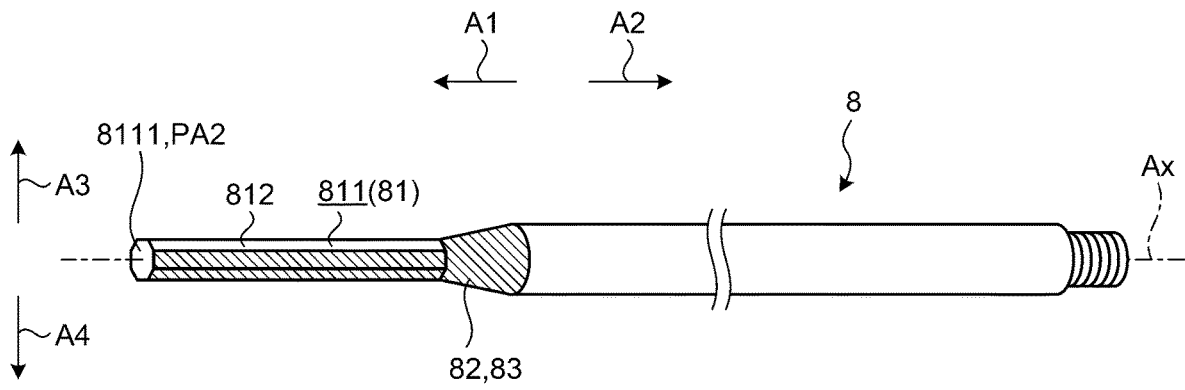
FIG. 3 is a perspective view illustrating a vibration transmission member.
Figure 4:
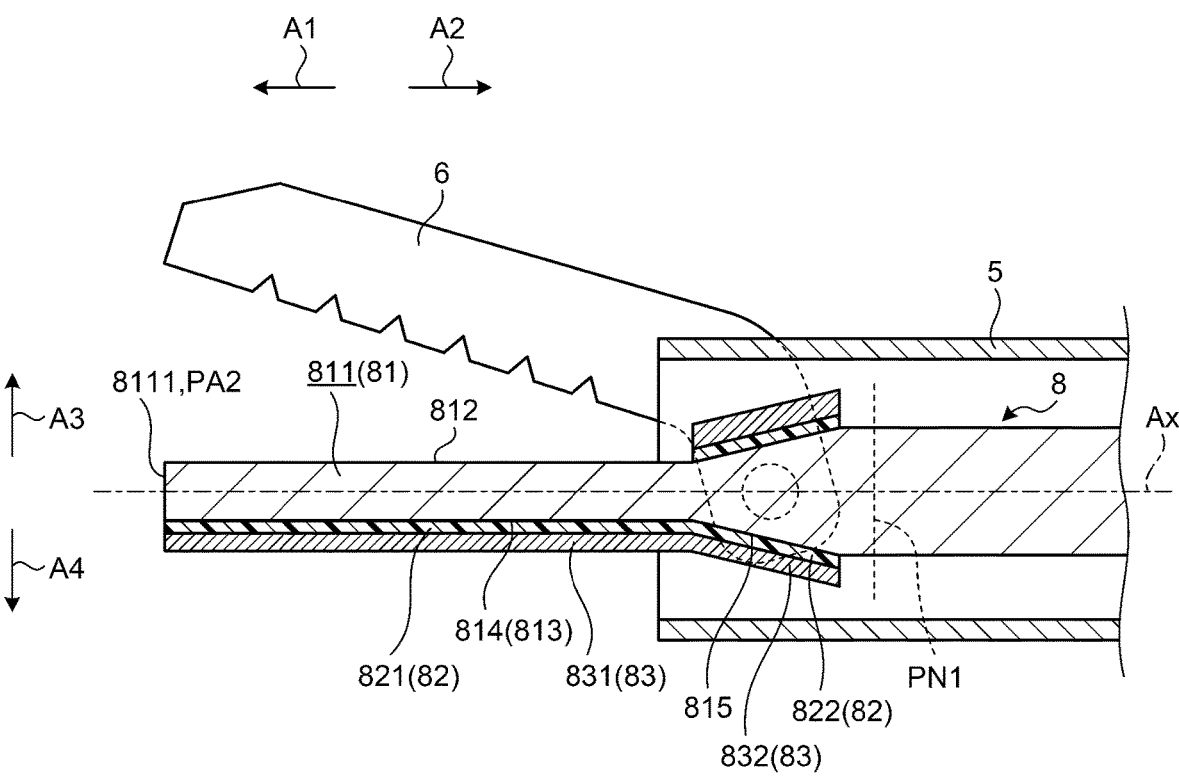
FIG. 4 is a cross-sectional view illustrating a portion of the vibration transmission member on a distal end side.
Figure 5:
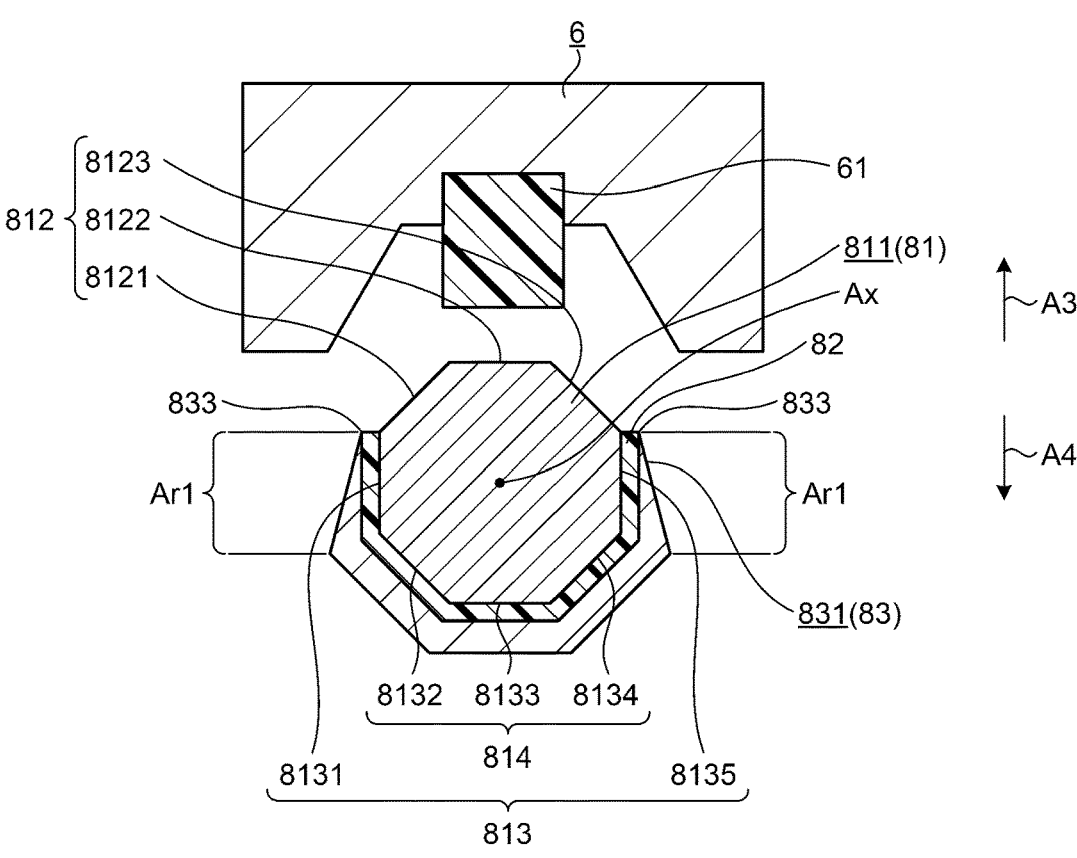
FIG. 5 is a cross-sectional view illustrating the portion of the vibration transmission member on the distal end side.

FIG. 3 is a perspective view illustrating the vibration transmission member 8. FIGS. 4 and 5 are cross-sectional views illustrating the portion of the vibration transmission member 8 on the distal end side A1. Specifically, FIG. 4 is a cross-sectional view of the vibration transmission member 8 taken along a plane including the central axis Ax and passing through a treatment surface 812. FIG. 5 is a cross-sectional view of the vibration transmission member 8 and the jaw 6 taken along a plane orthogonal to the central axis Ax and passing through a treatment portion 811.

Note that in the following description of the configuration of the vibration transmission member 8, the side close to the jaw 6 (the upper side in FIGS. 3 to 5) is referred to as a jaw side A3 (FIGS. 3 to 5), and the side away from the jaw 6 (the lower side in FIGS. 3 to 5) is referred to as a back surface side A4 (FIGS. 3 to 5).

As illustrated in FIGS. 3 to 5, the vibration transmission member 8 includes a main body 81, a coating 82 (which is a nonlimiting example of a first covering), and a mold portion 83 (which is a nonlimiting example of a second covering). Note that, in FIG. 3, for convenience of description, hatching is applied to positions where the coating 82 and the mold portion 83 are provided.

The main body 81 is formed of, for example, a titanium alloy or the like, and has an elongated shape extending linearly along the central axis Ax as illustrated in FIG. 3. Then, the main body 81 transmits the ultrasonic vibration, which has been generated by the ultrasonic transducer 72 and passed through the horn 73, from the end portion on the proximal end side A2 to the end portion on the distal end side A1.

Here, the main body 81, the horn 73, and the ultrasonic transducer 72 are one vibrator that performs longitudinal vibration by the ultrasonic vibration, which is generated by the ultrasonic transducer 72, at a predetermined resonance frequency. Therefore, a proximal end surface 734 (FIG. 2) of the horn 73 is positioned at a most proximal antinode position PA1 (FIG. 2) positioned on the most proximal end side A2 among the positions of antinodes of the longitudinal vibration. In addition, a distal end surface 8111 (FIGS. 3 and 4) of the main body 81 is positioned at a most distal antinode position PA2 (FIGS. 3 and 4) positioned on the most distal end side A1 among the positions of antinodes of the longitudinal vibration. Note that the longitudinal vibration has a frequency of, for example, 47 kHz and an amplitude of, for example, 80 μm at the most distal antinode position PA2.

In the main body 81, the end portion on the distal end side A1 functions as the treatment portion 811 which treats the target region in the state of gripping the target region between the main body and the jaw 6. The treatment portion 811 is a portion portioned on the distal end side A1 with respect to a most distal end node position PN1 (FIG. 4) portioned on the most distal end side A1 among the positions of nodes of the longitudinal vibration. Note that although not specifically illustrated, a lining for supporting the main body 81 with respect to the sheath 5 is provided at the most distal end node position PN1 between the main body 81 and the sheath 5. Then, a part of the treatment portion 811 is positioned in the state of protruding from the sheath 5 toward the distal end side A1.

In the first embodiment, as illustrated in FIG. 5, the treatment portion 811 has an octagonal shape in cross section, and is positioned in a posture in which three sides 8121 to 8123 having the octagonal shape in cross section face the jaw side A3. Then, the surfaces corresponding to the three sides 8121 to 8123 come into contact with the target region in a state where the target region is gripped between the treatment portion 811 and the jaw 6 and function as the treatment surface 812 for treating the target region. In addition, in the surfaces 813 corresponding to five sides 8131 to 8135 obtained by excluding the treatment surface 812 from the octagonal shape in cross section, the surfaces corresponding to three sides 8132 to 8134 are in a front and back relationship with the treatment surface 812. That is, the surfaces corresponding to the three sides 8132 to 8134 are positioned in a posture of facing the back surface side A4 and correspond to a back surface 814.

The coating 82 is a portion covering a part of the surface of the treatment portion 811, and is formed of a material having an electrical insulating property and a thermal conductivity lower than that of the main body 81. In the first embodiment, the coating 82 is formed of a material containing polyether ether ketone (PEEK) as a main component and containing a linear expansion adjustment filler having a linear expansion coefficient smaller than that of the main component with respect to the main component. Note that as the linear expansion adjustment filler, mica can be exemplified. In addition, the linear expansion adjustment filler is preferably contained in an amount of 0.1 mass % or more and 50 mass % or less.

Here, an area where the coating 82 is provided is as follows.

The coating 82 is provided in an area obtained by excluding the distal end surface 8111 and the treatment surface 812 from the treatment portion 811. That is, the coating 82 is provided on the surface 813 including the back surface 814. Hereinafter, in the coating 82, a portion provided on the surface 813 is referred to as a first coating 821 (FIG. 4). In addition, the coating 82 includes a second coating 822 (FIG. 4) connected to the first coating 821 on the proximal end side A2. The second coating 822 is positioned on the proximal end side in the treatment portion 811 and is provided on a surface 815 (FIG. 4) positioned inside the sheath 5. Then, the second coating 822 extends over the entire circumference of the surface 815 in a circumferential direction centered on the central axis Ax.

By using a material having an electrical insulating property and a thermal conductivity lower than that of the main body 81, the mold portion 83 is integrally formed on the coating 82 by, for example, insert molding or outsert molding. In the first embodiment, the mold portion 83 is formed of a material containing PEEK as a main component and containing a glass filler with respect to the main component. Note that the glass filler is preferably contained in an amount of 10 mass % or more and 40 mass % or less.

Here, an area where the mold portion 83 is provided is the same as the area where the coating 82 is provided. That is, as illustrated in FIG. 4, the mold portion 83 includes a first mold portion 831 provided on the entire first coating 821 and a second mold portion 832 provided on the entire second coating 822. Note that the mold portion 83 may be provided only on a part of the coating 82 without being provided on the entire coating 82.

Incidentally, in a case where the target region is gripped between the portion of the vibration transmission member 8 on the distal end side A1 and the jaw 6, the portion receives pressure from the jaw 6 toward the back surface side A4 with the most distal end node position PN1 supported by a lining (not illustrated) with respect to the sheath 5 as a fulcrum.

Therefore, a tensile stress is applied to the jaw side A3 in the portion of the vibration transmission member 8 on the distal end side A1. The tensile stress becomes larger toward the jaw side A3. That is, in the first mold portion 831, the end portion in the circumferential direction centered on the central axis Ax corresponds to a first area Ar1 (FIG. 5), which includes the region where the stress concentrates. In the first embodiment, the first area Ar1 is an area over the entire length in a direction along the central axis Ax in the first mold portion 831.

The thickness dimension of the first area Ar1 is set to be smaller than the thickness dimension of the area of the mold portion 83 other than the first area Ar1. In the first embodiment, the other area has a constant thickness dimension. Here, by securing a thickness dimension of 0.1 mm or more as the constant thickness dimension, it is possible to secure an excellent heat insulating property compared with a configuration in which only the coating 82 is provided. In addition, in order to ensure a moldability, it is more preferable to secure a thickness dimension of 0.2 mm or more as the constant thickness dimension. Furthermore, by setting the constant thickness dimension to a thickness dimension of 2.0 mm or less, it is possible to prevent an increase in size of the device and to secure an insertability into a trocar or the like. That is, the constant thickness dimension is preferably 0.1 mm or more and 2.0 mm or less. In addition, the constant thickness dimension is more preferably 0.2 mm or more and 1.0 mm or less. Further, the constant thickness dimension is larger than the thickness dimension of the coating 82. In addition, as illustrated in FIG. 5, the thickness dimension of the first area Ar1 decreases toward an end edge 833 in the circumferential direction centered on the central axis Ax.

Method of Manufacturing Vibration Transmission Member

Next, a method of manufacturing the above-described vibration transmission member 8 will be described.

Figure 6:
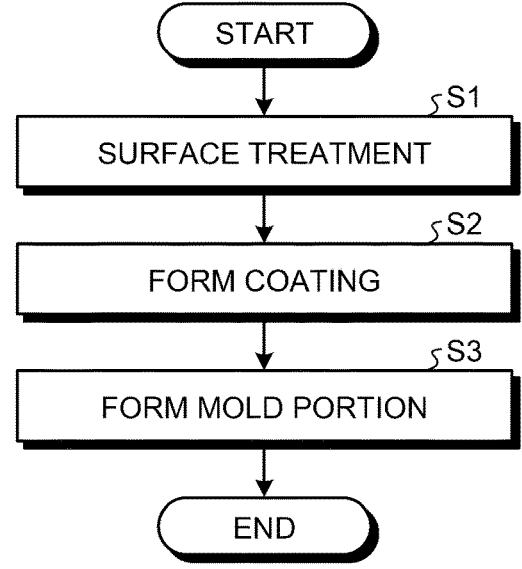
FIG. 6 is a flowchart illustrating a method of manufacturing the vibration transmission member.

FIG. 6 is a flowchart illustrating a method of manufacturing the vibration transmission member 8.

First, the operator performs a surface treatment on the surfaces 813 and 815 of the treatment portion 811 in order to improve an adhesion strength between the surfaces 813 and 815 and the coating 82 (Step S1).

As the surface treatment, a surface treatment for increasing a surface roughness by sandblasting can be exemplified.

After Step S1, the operator forms the coating 82 on the surface-treated surfaces 813 and 815 (Step S2).

Specifically, in Step S2, the operator blows, to the surfaces 813 and 815, a liquid containing the linear expansion adjustment filler (mica) having a scaly shape with respect to the main component (PEEK) having a granular shape. Then, the operator heats the liquid to form the coating 82.

Note that in the surface treatment in Step S1, an oxide film is removed from the surfaces 813 and 815, and an anchor effect and a stress effect from an uneven surface are applied in relation to the surfaces 813 and 815. As a result, the adhesion strength between the surfaces 813 and 815 and the coating 82 is improved.

After Step S2, the operator forms the mold portion 83 on the coating 82 (Step S3).

Figure 7:
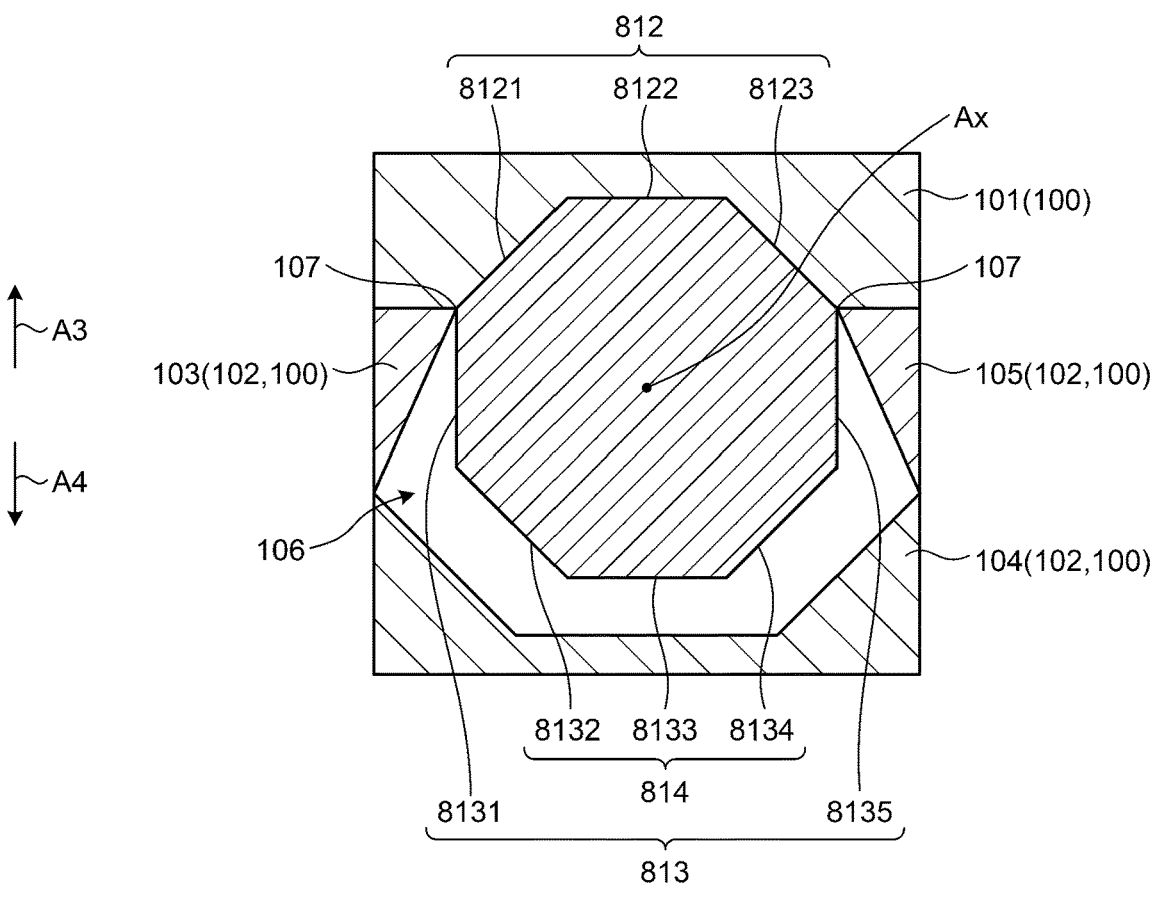
FIG. 7 is a view for explaining Step S3.

FIG. 7 is a view for explaining Step S3. Specifically, FIG. 7 corresponds to FIG. 5, and is a cross-sectional view of the main body 81 formed with the coating 82 and a mold 100 taken along the plane orthogonal to the central axis Ax. Note that in FIG. 7, the coating 82 is not illustrated for convenience of description.

Here, as illustrated in FIG. 7, the mold 100 includes an upper mold 101 and a lower mold 102 which are combined with each other. Note that the lower mold 102 includes first to third molds 103 to 105. Then, by combining the upper mold 101 and the lower mold 102, a cavity 106 corresponding to the outer shapes of the main body 81, the coating 82, and the mold portion 83 is provided in the mold 100. In addition, in a case where the main body 81 formed with the coating 82 is installed in the cavity 106, a hollow space of the cavity 106 excluding the main body 81 is narrowed toward an end edge 107 of the main body 81 in the circumferential direction centered on the central axis Ax.

Specifically, in Step S3, the operator installs the main body 81 formed with the coating 82 in the cavity 106. Next, the temperature of the mold 100 is set to a predetermined temperature. Here, the predetermined temperature can be, for example, a temperature equal to or higher than the glass transition point of the material forming the mold portion 83 and equal to or lower than the melting point of the material. Next, the molten material forming the mold portion 83 is injected into the cavity 106 to mold the mold portion 83. Here, the mold portion 83 and the coating 82 have the same main component. Therefore, when the mold portion 83 is molded by the above-described method, the mold portion 83 and the coating 82 are bonded to each other in such a manner that the main components are fused to each other. Note that when the molten material forming the mold portion 83 is injected into the cavity 106, it is preferable to set an injection pressure and an injection rate at the time of injection to be higher than a general injection pressure and a general injection rate in order to avoid the temperature of the molten material from being lowered by the mold 100.

According to the first embodiment described above, the following effects are obtained.

In the vibration transmission member 8 according to the first embodiment, the back surface 814 of the treatment portion 811 is covered with the coating 82, and the mold portion 83 is integrally formed on the coating 82. That is, the back surface 814 is covered with the coating 82 and the mold portion 83 having a thermal conductivity lower than that of the main body 81.

Therefore, even in a case where the back surface 814 of the vibration transmission member 8 on the side opposite to the treatment surface 812 comes into contact with a region of the living tissue other than the target region, the temperature rise of the back surface 814 is suppressed by the coating 82 and the mold portion 83, and thus, there is no unintended effect on the living tissue. In particular, since not only the coating 82 but also the mold portion 83 is provided, the thickness dimension of a portion having a thermal conductivity lower than that of the main body 81 can be increased. Therefore, the temperature rise of the back surface 814 can be further suppressed as compared with the configuration in which only the coating 82 is provided.

In addition, the coating 82 and the mold portion 83 are integrally formed with the main body 81. That is, there is no gap between the main body 81 and the coating 82, and the mold portion 83. Therefore, when treatment is performed by the ultrasonic treatment instrument 2, it is possible to prevent that the living tissue enters the gap so that the living tissue clogs the gap.

As described above, according to the vibration transmission member 8 of the first embodiment, it is possible to obtain a sufficient adhesion strength of the coating while avoiding an unintended effect on the living tissue.

In the vibration transmission member 8 according to the first embodiment, the coating 82 and the mold portion 83 are formed of a material having an electrical insulating property.

Therefore, the high frequency current flows intensively through a portion where the coating 82 and the mold portion 83 are not provided. On the other hand, since the coating 82 and the mold portion 83 are not provided in a range in contact with the target region, the high frequency current efficiently flows through the target region. In other words, it is possible to reduce the flow of the high frequency current to the living tissue and the like, which is positioned on the back surface side A4 of the treatment portion 811 on the side opposite to the treatment surface 812, other than the target region. As a result, it is possible to improve a treatment performance, shorten the time of the high frequency treatment, and reduce the invasion of an unnecessary high frequency current to the surrounding tissue.

In the vibration transmission member 8 according to the first embodiment, the thickness dimension of the first area Ar1 including the region of the mold portion 83 where the stress concentrates is set to a dimension smaller than the thickness dimension of the area of the mold portion 83 other than the first area Ar1.

Therefore, the first area Ar1 can be caused to follow the pressure received from the jaw 6 toward the back surface side A4 or the deformation of the main body 81 caused by the ultrasonic vibration. Therefore, the occurrence of cracks in the first area Ar1 can be suppressed.

In particular, in the first mold portion 831, the end portion in the circumferential direction centered on the central axis Ax is a region where the tensile stress corresponding to the pressure received from the jaw 6 toward the back surface side A4 increases. Therefore, by setting the first area Ar1 in this region, it is possible to suitably construct a structure for suppressing the occurrence of cracks in the mold portion 83.

In the vibration transmission member 8 according to the first embodiment, the thickness dimension of the first area Ar1 decreases toward the end edge 833 in the circumferential direction centered on the central axis Ax in the first mold portion 831.

Therefore, for example, as compared with a configuration in which the thickness dimension of the first area Ar1 is constant, the first area Ar1 can be accurately formed into a desired shape at the time of molding the mold portion 83. That is, the vibration transmission member 8 can be easily manufactured.

Second Embodiment

Next, a second embodiment will be described.

In the following description, the same reference numerals are given to the same configurations as those of the first embodiment described above, and a detailed description thereof will be omitted or simplified.

Figure 8:
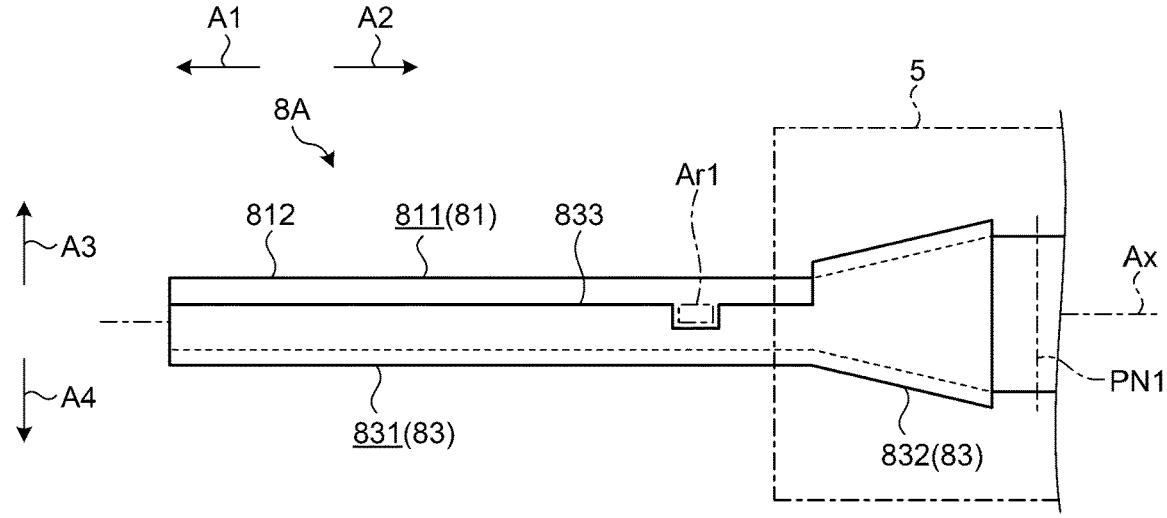
FIG. 8 is a view illustrating a portion of a vibration transmission member on the distal end side according to a second embodiment.
Figure 9:
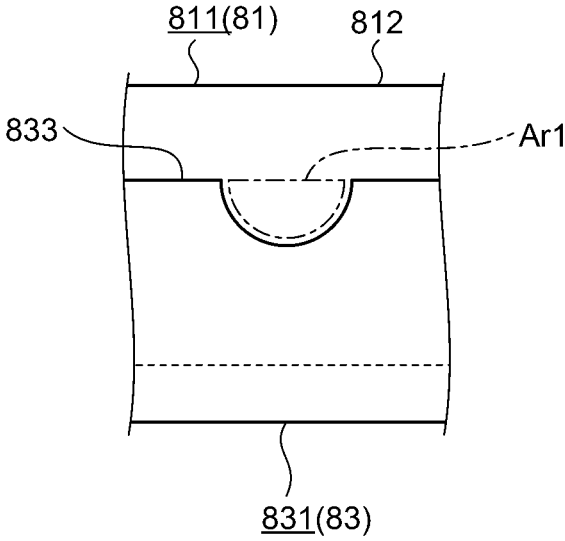
FIG. 9 is a view illustrating a modification of the second embodiment.
Figure 10:
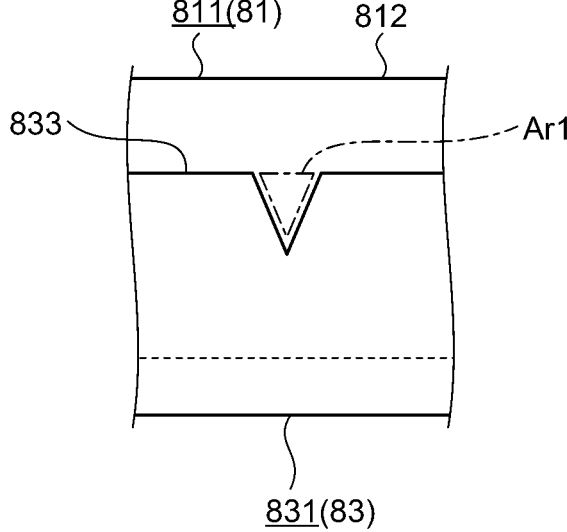
FIG. 10 is a view illustrating a modification of the second embodiment.
Figure 11:
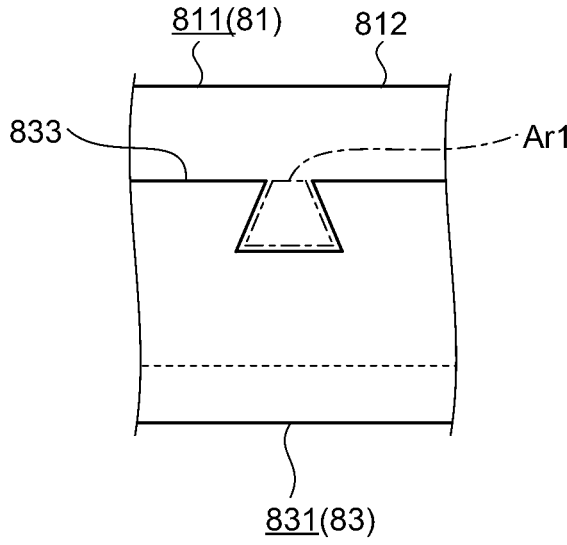
FIG. 11 is a view illustrating a modification of the second embodiment.
Figure 12:
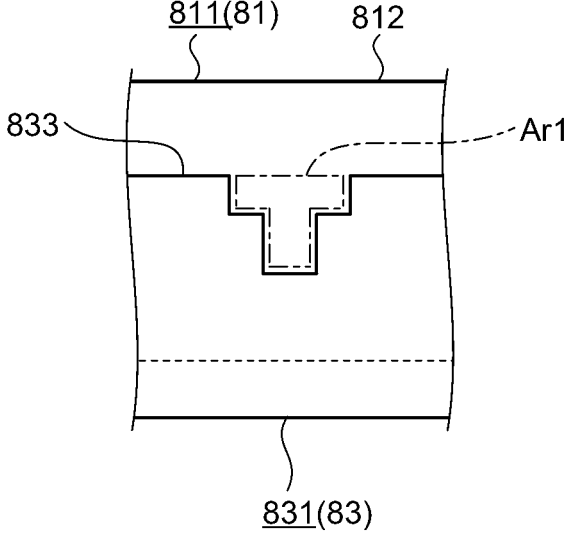
FIG. 12 is a view illustrating a modification of the second embodiment.

FIG. 8 is a view illustrating a portion of a vibration transmission member 8A on the distal end side A1 according to the second embodiment. Specifically, FIG. 8 is a side view of the vibration transmission member 8A as viewed from the same direction as the direction in which the vibration transmission member 8 is viewed in FIG. 4.

In the vibration transmission member 8A according to the second embodiment, as illustrated in FIG. 8, the position of the first area Ar1 is different from that of the vibration transmission member 8 described in the first embodiment described above.

Specifically, as illustrated in FIG. 8, the first area Ar1 is an end portion of the first mold portion 831 in the circumferential direction centered on the central axis Ax and is a partial area of the entire length in the direction along the central axis Ax.

Incidentally, as described in the first embodiment described above, the tensile stress applied to the portion of the vibration transmission member 8A on the distal end side A1 in a case where when the target region is gripped between the vibration transmission member and the jaw 6 increases toward the jaw side A3. In addition, the tensile stress increases toward the most distal end node position PN1. Furthermore, in the portion of the vibration transmission member 8A on the distal end side A1, a portion protruding from the sheath 5 toward the distal end side A1 is a portion which becomes high temperature at the time of treatment of the target region, and a crack is likely to occur due to the above-described tensile stress.

As described above, in the vibration transmission member 8A according to the second embodiment, as illustrated in FIG. 8, the first area Ar1 is set to be the end portion of the first mold portion 831 in the circumferential direction centered on the central axis Ax and the portion positioned on the proximal end side A2 in the portion protruding from the sheath 5 to the distal end side Ar1. In addition, In the second embodiment, the first area Ar1 is a rectangular area.

The mold portion 83 according to the second embodiment has a configuration in which the first area Ar1 is cut out. That is, the thickness dimension of the first area Ar1 is zero, and is smaller than the thickness dimension of the area of the mold portion 83 other than the first area Ar1. Note that the other area has a constant thickness dimension as in the first embodiment described above. In addition, the constant thickness dimension is preferably 0.1 mm or more and 2.0 mm or less, and more preferably 0.2 mm or more and 1.0 mm or less. Further, the constant thickness dimension is larger than the thickness dimension of the coating 82.

Here, in the coating 82 according to the second embodiment, the area corresponding to the above-described first area Ar1 may not be provided with the coating 82 similarly to the first area Ar1, or may be provided with the coating 82.

By using a mold in which the portion corresponding to the first area Ar1 has a different shape from that of the mold 100 described in the first embodiment described above, the vibration transmission member 8A according to the second embodiment is manufactured by the manufacturing method (FIG. 6) described in the first embodiment described above.

In addition, the thickness dimension of the first area Ar1 according to the second embodiment is not limited to zero and may be a predetermined thickness dimension as long as the thickness dimension is smaller than the thickness dimension of the area of the mold portion 83 other than the first area Ar1.

Even in a case where the first area Ar1 is set as in the second embodiment described above, the same effects as those of the first embodiment described above are obtained.

Modification of Second Embodiment

FIGS. 9 to 14 are views illustrating modifications of the second embodiment. Specifically, FIGS. 9 to 14 are views corresponding to FIG. 8. Note that in FIGS. 9 to 13, only the periphery of the first area Ar1 is enlarged for convenience of description.

Figure 13:
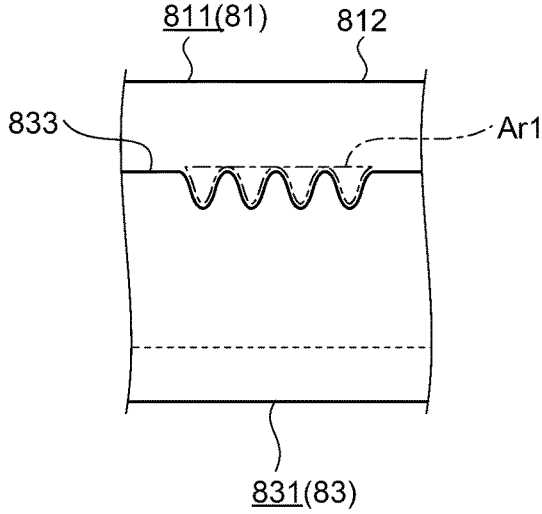
FIG. 13 is a view illustrating a modification of the second embodiment.

In the second embodiment described above, the first area Ar1 is configured by a rectangular area, but the disclosure is not limited thereto. For example, the first area Ar1 may be configured by a semicircular area (FIG. 9), a triangular area (FIG. 10), a trapezoidal area (FIG. 11), a T-shaped area (FIG. 12), or an area where the end edge 833 is wavy (FIG. 13).

Figure 14:
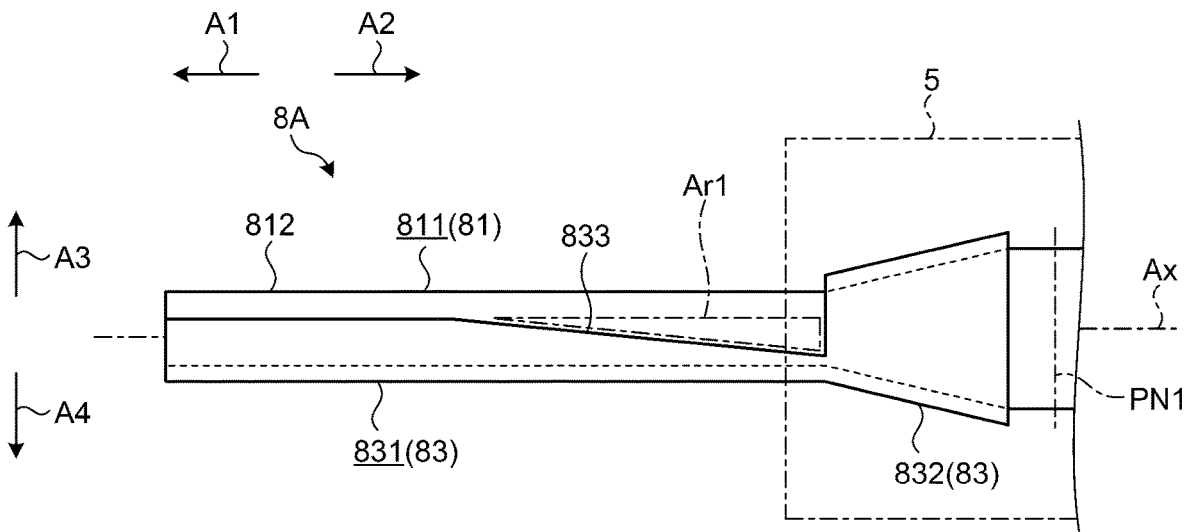
FIG. 14 is a view illustrating a modification of the second embodiment.

As described in the second embodiment described above, the tensile stress applied to the portion of the vibration transmission member 8A on the distal end side A1 in a case where the target region is gripped between the vibration transmission member and the jaw 6 increases toward the jaw side A3 and increases toward the most distal end node position PN1. Therefore, as illustrated in FIG. 14, the first area Ar1 may be configured by a triangular area in which the end edge 833 is inclined to the back surface side A4 toward the proximal end side A2.

Third Embodiment

Next, a third embodiment will be described.

In the following description, the same reference numerals are given to the same configurations as those of the first embodiment described above, and a detailed description thereof will be omitted or simplified.

Figure 15:
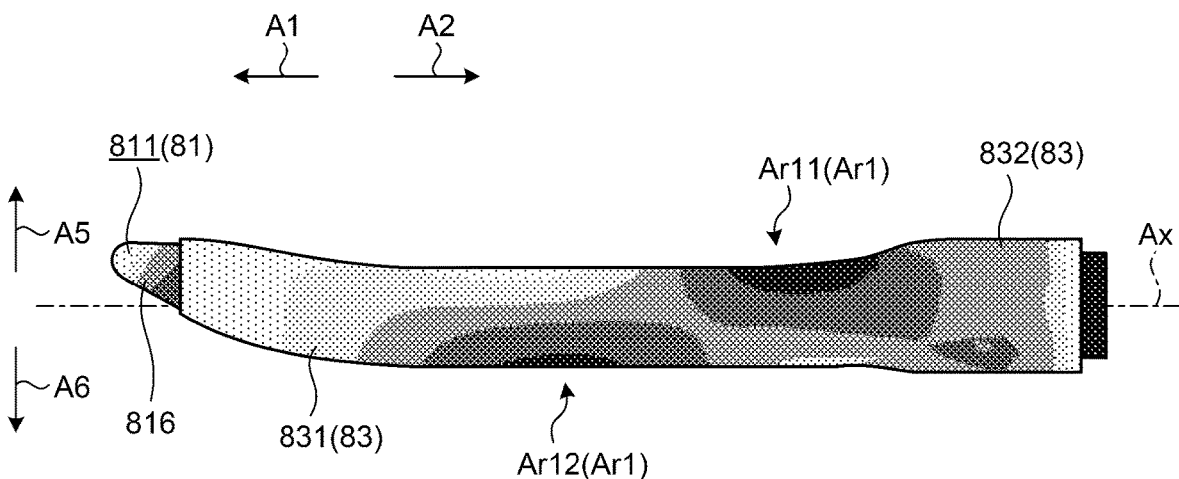
FIG. 15 is a view for explaining a configuration of a vibration transmission member according to a third embodiment.
Figure 16:
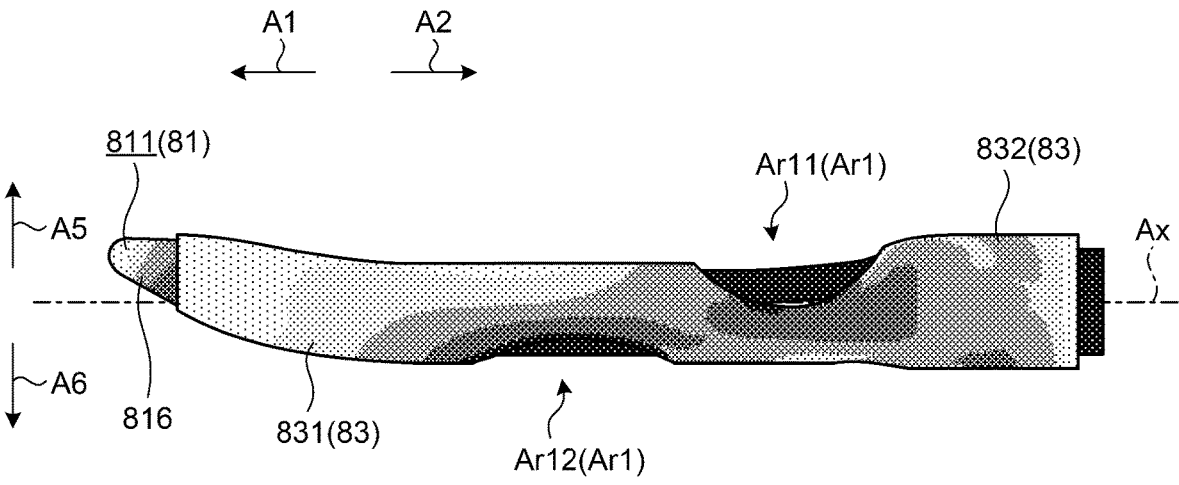
FIG. 16 is a view for explaining the configuration of the vibration transmission member according to the third embodiment.

FIGS. 15 and 16 are views for explaining a configuration of a vibration transmission member 8B according to the third embodiment. Specifically, FIG. 15 is a view illustrating the first area Ar1 according to the third embodiment, and illustrates a state where the first area Ar1 is not cut for convenience of description. FIG. 16 is a view illustrating the portion of the vibration transmission member 8B on the distal end side A1. Note that FIGS. 15 and 16 are views as viewed from the back surface side A4. In addition, In FIGS. 15 and 16, a vertical direction is orthogonal to a longitudinal direction (central axis Ax) of the main body 81 and a direction in which the treatment surface 812 and the back surface 814 face each other, and corresponds to a width direction. Hereinafter, in the width direction, in FIGS. 15 and 16, the upper side is referred to as a first direction A5, and the lower side is referred to as a second direction A6.

In the vibration transmission member 8B according to the third embodiment, as illustrated in FIG. 15 or 16, the shape of the treatment portion 811 is changed with respect to the vibration transmission member 8 described in the first embodiment described above.

Specifically, as illustrated in FIG. 15 or 16, the treatment portion 811 according to the third embodiment is curved in the first direction A5 unlike the treatment portion 811 described in the first embodiment described above. Hereinafter, for convenience of description, a region curved in the first direction A5 in the treatment portion 811 will be referred to as a curved portion 816 (FIGS. 15 and 16).

Note that the vibration transmission member 8B is different from the treatment portion 811 described in the first embodiment described above only in that the treatment portion 811 is curved, and an area where the coating 82 and the mold portion 83 are provided is the area similar to the first embodiment described above.

Incidentally, in a case where the treatment portion 811 has the above-described curved portion 816, when the vibration transmission member 8B is caused to generate a longitudinal vibration by driving the ultrasonic transducer 72, the stress generated in the mold portion 83 has distributions illustrated in FIGS. 15 and 16. Note that in FIGS. 15 and 16, the stress is expressed by shading of a pattern. Specifically, it is indicated that the stress increases when the pattern becomes darker.

In the vibration transmission member 8B according to the third embodiment, as illustrated in FIGS. 15 and 16, two regions (first areas Ar1) of the mold portion 83 where the stress concentrates are provided. Hereinafter, one of the two first areas Ar1 will be referred to as a proximal end side area Ar11, and the other will be referred to as a distal end side area Ar12.

The proximal end side area Ar11 is provided on the first direction A5 side.

On the other hand, the distal end side area Ar12 is provided on the second direction A6 side. In addition, the distal end side area Ar12 is provided on the distal end side A1 of the proximal end side area Ar11, and is provided on the proximal end side A2 of the curved portion 816.

The mold portion 83 according to the third embodiment has a configuration in which the first area Ar1 is cut out. That is, the thickness dimension of the first area Ar1 is zero, and is smaller than the thickness dimension of the area of the mold portion 83 other than the first area Ar1. Then, the proximal end side area Ar11 corresponds to a first cutout. In addition, the distal end side area Ar12 corresponds to a second cutout. Note that the other area has a constant thickness dimension as in the first embodiment described above. In addition, the constant thickness dimension is preferably 0.1 mm or more and 2.0 mm or less, and more preferably 0.2 mm or more and 1.0 mm or less. Further, the constant thickness dimension is larger than the thickness dimension of the coating 82.

Here, in the coating 82 according to the third embodiment, the area corresponding to the above-described first area Ar1 may not be provided with the coating 82 similarly to the first area Ar1, or may be provided with the coating 82.

By using a mold in which the portion corresponding to the first area Ar1 has a different shape from that of the mold 100 described in the first embodiment described above, the vibration transmission member 8B according to the third embodiment is manufactured by the manufacturing method (FIG. 6) described in the first embodiment described above.

In addition, the thickness dimension of the first area Ar1 according to the third embodiment is not limited to zero and may be a predetermined thickness dimension as long as the thickness dimension is smaller than the thickness dimension of the area of the mold portion 83 other than the first area Ar1.

Even in a case where the first area Ar1 is set as in the third embodiment described above, the same effects as those of the first embodiment described above are obtained.

Fourth Embodiment

Next, a fourth embodiment will be described.

In the following description, the same reference numerals are given to the same configurations as those of the first embodiment described above, and a detailed description thereof will be omitted or simplified.

Figure 17:
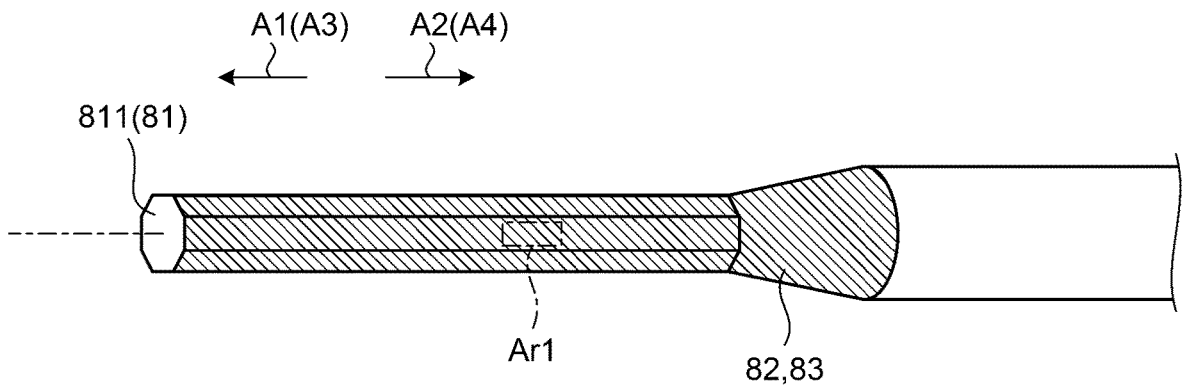
FIG. 17 is a view illustrating a portion of a vibration transmission member on the distal end side according to a fourth embodiment.
Figure 18:
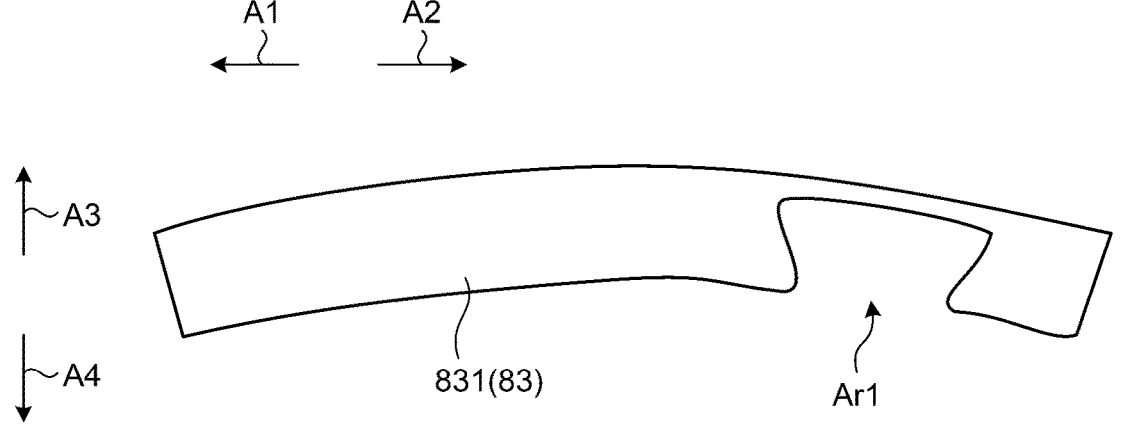
FIG. 18 is a view for explaining a function of a first area.

FIG. 17 is a view illustrating a portion of a vibration transmission member 8C on the distal end side A1 according to the fourth embodiment. Note that FIG. 17 is a view of the portion of the vibration transmission member 8C on the distal end side A1 as viewed from the back surface side A4. In addition, in FIG. 17, as in FIG. 3, hatching is applied to the positions where the coating 82 and the mold portion 83 are provided. FIG. 18 is a view for explaining the function of the first area Ar1. Note that FIG. 18 illustrates a state where the first mold portion 831 is curved toward the back surface side A4 by gripping the target region between the portion of the vibration transmission member 8C on the distal end side A1 and the jaw 6 and applying a pressure from the jaw 6 toward the back surface side A4 to the portion of the vibration transmission member 8C on the distal end side A1.

In the vibration transmission member 8C according to the fourth embodiment, as illustrated in FIG. 17, the position of the first area Ar1 is different from that of the vibration transmission member 8 described in the first embodiment described above.

Specifically, as illustrated in FIG. 17, the first area Ar1 is a partial area, which is positioned on the back surface side A4, in the first mold portion 831.

As illustrated in FIG. 18, the thickness dimension of the first area Ar1 is set to be smaller than the thickness dimension of the area of the mold portion 83 other than the first area Ar1. Note that the other area has a constant thickness dimension as in the first embodiment described above. In addition, the constant thickness dimension is preferably 0.1 mm or more and 2.0 mm or less, and more preferably 0.2 mm or more and 1.0 mm or less. Further, the constant thickness dimension is larger than the thickness dimension of the coating 82.

Incidentally, as illustrated in FIG. 18, a case is assumed in which the first mold portion 831 is curved toward the back surface side A4 by applying a pressure from the jaw 6 toward the back surface side A4 to the portion of the vibration transmission member 8C on the distal end side A1. In this case, a compressive stress is applied to the back surface side A4 of the first mold portion 831. When the thickness dimension of the first mold portion 831 is large, the compressive stress becomes large according to the thickness dimension. Then, due to the compressive stress, a crack is likely to occur at any position of the first mold portion 831. That is, the first area Ar1 according to the fourth embodiment has a function of suppressing the occurrence of cracks in the first mold portion 831 by relaxing the above-described compressive stress.

By using a mold in which the portion corresponding to the first area Ar1 has a different shape from that of the mold 100 described in the first embodiment described above, the vibration transmission member 8C according to the fourth embodiment is manufactured by the manufacturing method (FIG. 6) described in the first embodiment described above.

In addition, the thickness dimension of the first area Ar1 according to the fourth embodiment may be zero as long as the thickness dimension is smaller than the thickness dimension of the area of the mold portion 83 other than the first area Ar1.

Even in a case where the first area Ar1 is set as in the fourth embodiment described above, the same effects as those of the first embodiment described above are obtained.

OTHER EMBODIMENTS

Although the embodiments for carrying out the disclosure have been described so far, the disclosure should not be limited only by the first to fourth embodiments described above.

In the first to fourth embodiments described above, the shape of the treatment portion 811 is not limited to the octagonal shape in cross section, and another shape such as a circular shape in cross section may be adopted.

In the first to fourth embodiments described above, the first area Ar1 is formed by molding the mold portion 83, but the disclosure is not limited thereto. For example, the first area Ar1 may be formed by performing cutting or the like after molding the mold portion 83.

In the first to fourth embodiments described above, both the ultrasonic energy and the high frequency energy are applied to the target region, but the disclosure is not limited thereto, and only the ultrasonic energy may be applied to the target region. In addition, at least one energy of the high frequency energy and thermal energy by a heater or the like and the ultrasonic energy may be applied to the target region.

According to the vibration transmission member, the ultrasonic treatment instrument, and the method of manufacturing the vibration transmission member according to the disclosure, it is possible to obtain a sufficient adhesion strength of a coating while avoiding an unintended effect on a living tissue.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A vibration transmission member comprising:
a main body configured to transmit ultrasonic vibration;
a treatment portion located at the distal end of the main body, the treatment portion configured to apply ultrasonic vibration to a living tissue;
a first covering formed of a material that has an electrical insulating property and has a thermal conductivity lower than a thermal conductivity of the main body, the first covering covering a part of a surface of the treatment portion; and
a second covering formed of a material that has an electrical insulating property and has a thermal conductivity lower than the thermal conductivity of the main body, the second covering located on the first covering, wherein
the second covering includes a first area and a second area, the first area located adjacent to the second area in a circumferential direction of the main body and disposed closer to a jaw side than the second area is, and
a thickness of the first area is smaller than a thickness of the second area,
the treatment portion includes:
a treatment surface configured to apply the ultrasonic vibration to the living tissue, and
a back surface opposite to the treatment surface, and
the first covering and the second covering cover the surface of the treatment portion which excludes the treatment surface and includes at least the back surface.

2. The vibration transmission member according to claim 1, wherein the first area is at least a part of an end portion of the second covering in the circumferential direction, which is centered on a central axis along a longitudinal direction of the main body.

3. The vibration transmission member according to claim 2, wherein the thickness of the first area decreases toward an end edge of the second covering in the circumferential direction.

4. The vibration transmission member according to claim 1, wherein the treatment portion includes
a curved portion that is curved in a width direction orthogonal to each of a longitudinal direction of the main body and a direction in which the treatment surface and the back surface face each other.

5. The vibration transmission member according to claim 4, wherein when the width direction is defined such that a direction in which the curved portion is curved is a first direction, and a direction opposite to the first direction is a second direction, the first area includes:
a first cutout provided on a side of the first direction and the first cutout has a thickness of zero, and
a second cutout provided on a side of the second direction and the second cutout has a thickness of zero.

6. The vibration transmission member according to claim 5, wherein the second cutout is provided on a distal end side of the first cutout.

7. The vibration transmission member according to claim 6, wherein the second cutout is provided on a proximal end side of the curved portion.

8. The vibration transmission member according to claim 1, wherein the second covering is a mold portion that is formed by mold processing.

9. The vibration transmission member according to claim 1, wherein a thickness of a first part of the first area that is relatively closer to the second area is thicker than a thickness of a second part of the first area that is relatively farther far from the second area.

10. The vibration transmission member according to claim 9, wherein the first area includes a region where stress concentrates.

11. The vibration transmission member according to claim 1, wherein the first area includes a region where stress concentrates.

12. The vibration transmission member according to claim 1, wherein the second covering includes a glass filler.

13. An ultrasonic treatment instrument comprising:
a vibration transmission member configured to transmit ultrasonic vibration; and
a jaw configured to grip a living tissue between the jaw and the vibration transmission member, wherein:
the vibration transmission member includes:
a main body configured to transmit the ultrasonic vibration,
a treatment portion located at the distal end of the main body, the treatment portion being configured to grip the living tissue between the treatment portion and the jaw, and the treatment portion configured to apply the ultrasonic vibration to the living tissue,
a first covering formed of a material that has an electrical insulating property and has a thermal conductivity lower than a thermal conductivity of the main body, the first covering covering a part of a surface of the treatment portion, and
a second covering formed of a material that has an electrical insulating property and has a thermal conductivity lower than the thermal conductivity of the main body, the second covering located on the first covering, wherein
the second covering includes a first area and a second area, the first area located adjacent to the second area in a peripheral direction of the main body and disposed closer to a jaw side than the second area is,
a thickness of the first area is smaller than a thickness of the second area,
the treatment portion includes:
a treatment surface configured to apply the ultrasonic vibration to the living tissue, and
a back surface opposite to the treatment surface, and
the first covering and the second covering cover the surface of the treatment portion which excludes the treatment surface and includes at least the back surface.

14. The vibration transmission member according to claim 13, wherein a thickness of a first part of the first area that is relatively closer to the second area is thicker than a thickness of a second part of the first area that is relatively farther far from the second area.

15. The vibration transmission member according to claim 14, wherein the first area includes a region where stress concentrates.

16. The vibration transmission member according to claim 13, wherein the second covering includes a glass filler.

17. A vibration transmission member comprising:

a main body configured to transmit ultrasonic vibration;

a treatment portion located at the distal end of the main body, the treatment portion configured to apply ultrasonic vibration to a living tissue, the treatment portion including a curved portion curved in a first direction;

a first covering formed of a material that has an electrical insulating property and has a thermal conductivity lower than a thermal conductivity of the main body, the first covering covering a part of a surface of the treatment portion; and a second covering formed of a material that has an electrical insulating property and has a thermal conductivity lower than the thermal conductivity of the main body, the second covering located on the first covering, wherein the second covering includes a first area and a second area, the first area located adjacent to the second area in a peripheral direction of the main body, and a thickness of the first area is smaller than a thickness of the second area, the first area includes a first cutout and a second cutout, the first cutout is located in a side of the first direction, and the second cutout is located in a side of a second direction opposed to the first direction.

18. The vibration transmission member according to claim 17, wherein a thickness of a first part of the first area that is relatively closer to the second area is thicker than a thickness of a second part of the first area that is relatively farther far from the second area.

19. The vibration transmission member according to claim 18, wherein the first area includes a region where stress concentrates.

\* \* \* \* \*